United States Patent
Akolkar et al.

(10) Patent No.: US 11,125,717 B2
(45) Date of Patent: Sep. 21, 2021

(54) ELECTROCHEMICAL SENSOR FOR LEAD DETECTION

(71) Applicant: CASE WESTERN RESERVE UNIVERSITY, Cleveland, OH (US)

(72) Inventors: Rohan Akolkar, Beachwood, OH (US); Xinyu Liu, Cleveland, OH (US); Kailash Venkatraman, Beachwood, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 41 days.

(21) Appl. No.: 16/255,486

(22) Filed: Jan. 23, 2019

(65) Prior Publication Data
US 2019/0227030 A1    Jul. 25, 2019

Related U.S. Application Data

(60) Provisional application No. 62/620,786, filed on Jan. 23, 2018.

(51) Int. Cl.
*G01N 27/416* (2006.01)
*G01N 27/42* (2006.01)

(52) U.S. Cl.
CPC ........ *G01N 27/4166* (2013.01); *G01N 27/42* (2013.01)

(58) Field of Classification Search
None
See application file for complete search history.

(56) References Cited

PUBLICATIONS

L. T. Viyannalage, et al. "Electrochemical Method for Quantitative Determination of Trace Amounts of Lead", Analytical Chemistry, 80(6): p. 2042-2049, Mar. 15 (Year: 2008).*
S. Venugopalan, "Kinetics of hydrogen-evolution reaction on lead and lead-alloy electrodes in sulfuric acid electrolyte with phosphoric acid and antimony additives", vol. 48, Issue 3, Mar. 19, 1994, pp. 371-384.
Kirowa-Eisner, et al., "Journal of Electroanalytical Chemistry", vol. 552, Jul. 30, 2003, pp. 171-183.
Vasilic, et al., "Open circuit stability of underpotentially deposited Pb monolayer on Cu(111)", Journal of Electroanalytical Chemistry 580 (2005) 203-212.
Kang, et al., "Determination of Lead with Copper-Based Electrochemical Sensor", Anal Chem. Mar. 21, 2017; 89(6): 3345-3352.

(Continued)

*Primary Examiner* — J. Christopher Ball
(74) *Attorney, Agent, or Firm* — Tarolli, Sundheim, Covell & Tummino LLP

(57) ABSTRACT

A sensor for detecting lead in an aqueous solution includes a copper working electrode, a counter electrode, a power supply for applying underpotential deposition of lead onto the copper electrode from the aqueous solution, a measuring device for providing measurement of a hydrogen evolution reaction (HER) current on the $Pb_{upd}$-modified electrode, and a means for correlating the degree of suppression of the HER current to $Pb_{upd}$ coverage to determine the lead coverage and lead concentration of the solution.

14 Claims, 8 Drawing Sheets

(56) References Cited

PUBLICATIONS

Kim, et al., "Fluorescent and colorimetric sensors for detection of lead, cadmium, and mercury ions", Chem Soc Rev., Apr. 21, 2012;41(8):3210-44.

Bonfil, et al., "Analytics Chimica Acta", vol. 457, Issue 2, Apr. 22, 2002, pp. 285-296.

Dai, et al., "A Simple, Cost-Effective Sensor for Detecting Lead Ions inWater Using Under-Potential Deposited Bismuth Sub-Layer with Differential Pulse Voltammetry (DPV)", Sensors 2017, 17, 950, pp. 1-11.

Wuilloud, et al., "Determination of Lead in Drinking Water by ICP-AES With Ultrasonic Nebulization and Flow-Injection On-Line Preconcentration Using an Amberlite XAD-16 Resin", Analytical Letters, 35(10), 1649-1665 (2002).

Bertenshaw, et al., "Determination of lead in drinking water by atomic-absorption spectrophotometry with electrothermal atomisation", Issue 1258, 1981.

* cited by examiner

ELECTROCHEMICAL SENSOR FOR LEAD DETECTION

RELATED APPLICATION

This application claims priority from U.S. Provisional Application No. 62/620,786, filed Jan. 23, 2018, the subject matter of which is incorporated herein by reference in its entirety.

BACKGROUND

Lead contamination in drinking water is a worldwide problem affecting people in developing as well as developed countries. While lead contamination levels are routinely monitored at water treatment facilities, many water sources get contaminated with lead during distribution (lead pipes). The Environmental Protection Agency (EPA) has issued a regulation that limits the amount of lead concentration in drinking water to below 15 ppb. To ensure that drinking water is not lead contaminated, different methods are applied for detecting lead concentration in water. The most common methods include colorimetry, atomic absorption spectroscopy (AAS) and inductively coupled plasma (ICP) emission spectroscopy. These techniques can measure the lead concentration accurately; however, these methods are expensive and require access to advanced instrumentation, which is accessible only through certified laboratories. Therefore, it is essential to develop a low-cost, portable and reliable lead sensor for use in homes and offices.

SUMMARY

Embodiments described herein relate to a sensor and method for detecting, identifying, quantifying, and/or determining the amount or concentration of lead in an aqueous solution, and particularly relates to a sensor for detecting, identifying, quantifying, and/or determining the amount or concentration of lead in an aqueous solution, such as water or other fluids. Advantageously, the sensor enables detection of ppb-levels of lead in water.

The sensor includes a copper working electrode, a counter electrode, a power supply, and a current measuring device. The copper working electrode and counter electrode are configured for placement in the aqueous solution. The power supply is configured to apply underpotential deposition of lead onto the copper electrode from the aqueous solution. The measuring device provides measurement of a hydrogen evolution reaction (HER) current on the lead underpotential ($Pb_{upd}$)-modified electrode. The sensor can also include a means for correlating the degree of suppression of the HER current to $Pb_{upd}$ coverage to determine the lead coverage and lead concentration of the solution.

The sensor works on the principle of $Pb_{upd}$ form the aqueous solution onto the copper electrode followed by measurement of the hydrogen evolution reaction (HER) current on the $Pb_{upd}$-modified electrode surface. The degree of suppression of the HER current is correlated to $Pb_{upd}$ coverage, which in turn depends on the lead concentration in solution. The HER current of the $Pb_{upd}$ covered electrode can be compared to the HER baseline current on lead-free electrode to determine the lead coverage and thus the lead concentration of the solution.

In some embodiments, the sensor can include a substrate, a copper working electrode formed on a surface of the substrate, and a counter electrode formed on the surface of the substrate. The counter electrode can include a metalized film, such as gold, platinum, palladium, silver, carbon, alloys thereof, and composites thereof. The films used to form the working electrode and counter electrode can be provided on the surface of the substrate by film printing or sputtering or coating the films on the surface and then optionally laser ablating the films to form the working electrode and counter electrode.

In some embodiment, the copper working electrode can have an irregular needle-like dendrite surface profile that is defined by underlying dendrites of electrodeposited zinc. A sensor as described herein with a copper working with the dendrite surface profile can have decreased lead sensing time compared to sensor with a copper electrode having a planar surface.

DETAILED DESCRIPTION

Unless specifically addressed herein, all terms used have the same meaning as would be understood by those of skilled in the art of the subject matter of the application. The following definitions will provide clarity with respect to the terms used in the specification and claims.

As used herein, the term "quantitative data" or "quantitative level" or "quantitative amount" refers to data, levels, or amounts associated with any dataset components (e.g., markers, clinical indicia,) that can be assigned a numerical value.

As used herein, the terms "control" or "control sample" refer to one or more samples in which the concentration of the lead is known.

Embodiments described herein relate to an electrochemical sensor and method for detecting, identifying, quantifying, and/or determining the amount or concentration of lead in a sample, and particularly relates to a sensor for detecting, identifying, quantifying, and/or determining the amount or concentration of lead in a sample, such as tap or drinking water or other aqueous fluids.

Figure 1:
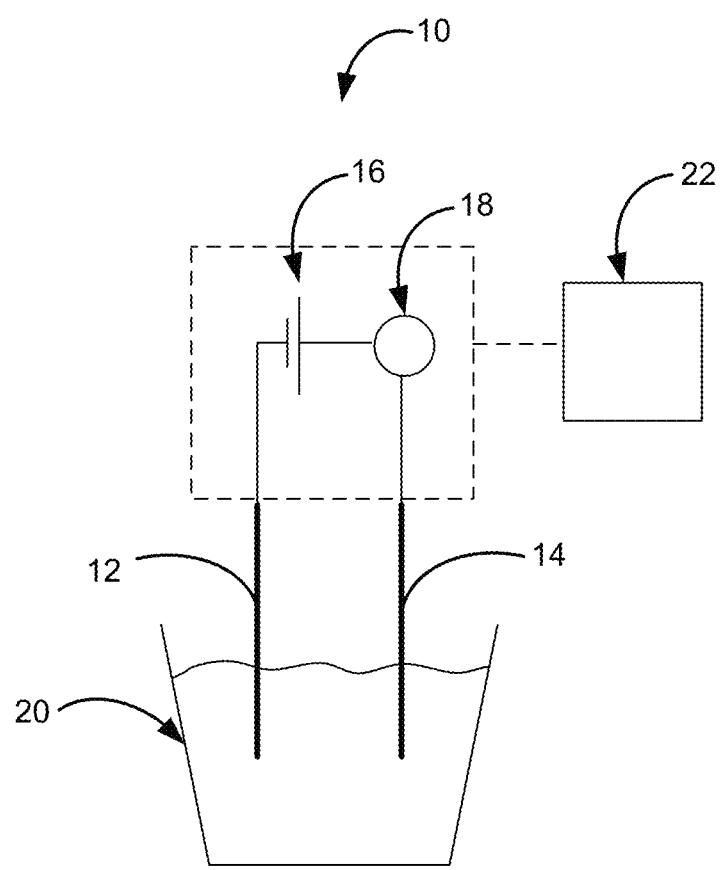
FIG. 1 is a schematic of an electrochemical sensor in accordance with an embodiment described herein.

FIG. 1 is a schematic illustration of an embodiment of the sensor 10 described herein. The sensor 10 includes a copper working electrode 12, a counter electrode 14, a power supply 16, and a current measuring device 18. The copper working electrode 10 and counter electrode 12 are configured for placement in an aqueous solution 20. The power supply 16 is configured to apply underpotential deposition of lead onto the copper working electrode 12 from the aqueous solution 20. The measuring device 18 (e.g., ammeter) provides measurement of a hydrogen evolution reaction (HER) current on the $Pb_{upd}$-modified working electrode 12. The sensor 10 can also include a means 22 for correlating the degree of suppression of the HER current to $Pb_{upd}$ coverage to determine the lead coverage and lead concentration of the solution.

In some embodiments, the electrochemical sensor 10 can include a reference electrode (not shown) and a measuring device (not shown) for applying voltage potentials to the working electrode and counter electrode and measuring the hydrogen evolution current of the lead covered working electrode and the hydrogen evolution baseline current on lead-free electrode to determine the level of the lead in a sample, such as a drinking water.

Figure 2:
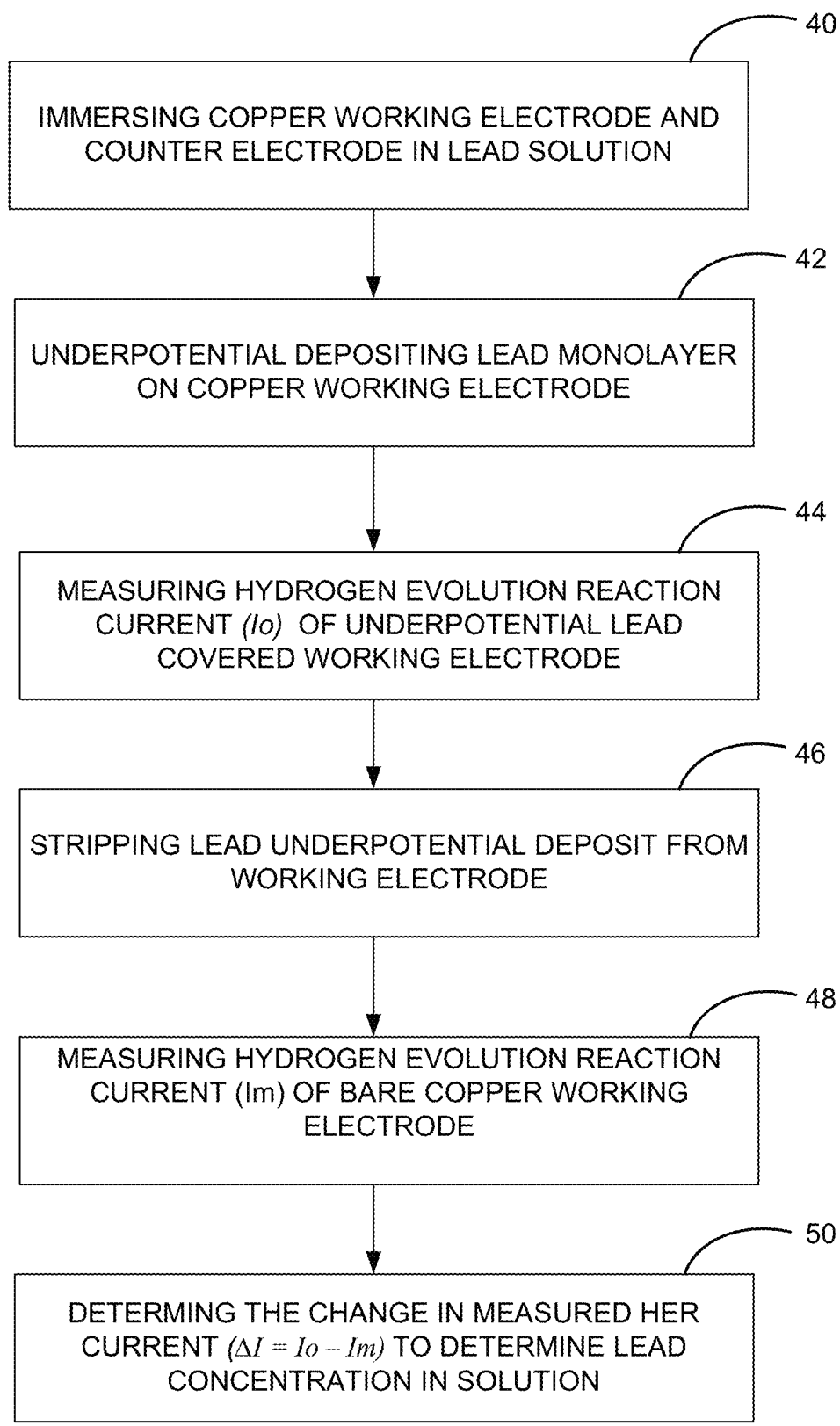
FIG. 2 is a flow chart illustrating a method of measuring lead concentrations in a sample using an electrochemical sensor as described herein.

FIG. 2 is a flow chart illustrating a method of measuring lead concentrations in a sample, such as drinking water, using an electrochemical sensor as described herein. In the method, at 40, a copper working electrode and counter electrode of the sensor is immersed in a lead-contaminated solution. At 42, the copper electrode is biased at a suitable (cathodic) potential that facilitates underpotential deposition of a lead monolayer on the copper surface of the working electrode. The coverage of the lead on the copper surface depends on time and the lead ion ($Pb^{+2}$) concentration in the sample. As lead covers the copper surface, it suppresses the ability of the surface to electrolyze water and evolve hydrogen gas. At 44, the hydrogen evolution reaction (HER) current of the underpotential lead covered electrode is then measured. Following measurement of the hydrogen evolution current of the underpotential lead covered electrode, at 46, the underpotentially deposited lead can be stripped to recover the bare copper surface of the working electrode. At 48, the HER baseline current (Io) on the blank (Pb-free) copper electrode is then measured. At 50, the change in hydrogen evolution current $\Delta I=Io-Im$ is calculated to determine the concentration of lead in the sample. For a given underpotential deposition time, higher lead concentration in the sample provides a larger lead underpotential deposition coverage on the copper working electrode, and thus a larger suppression of the hydrogen evolution current.

By way of example, an electrochemical sensor was provided that included a Cu wafer with surface area of 1 cm$^2$ as the working electrode, and Ag/AgCl electrode as the reference electrode, and a Pt wire as the counter electrode. Electrolytes were prepared utilizing deionized water with 10 mM perchloric acid and with varying concentrations of $Pb^{2+}$ (10 ppb-1 ppm). A potentiostat with data acquisition was used for the electrochemical measurements.

The pre-cleaned copper working electrode was immersed into the $Pb^{+2}$-containing electrolyte. Underpotential deposition (UPD) of lead was performed on the copper surface at an applied potential of −0.4 V vs. Ag/AgCl for a set time period t. After lead UPD surface coverage on Cu increased (surface coverage depends on UPD time t and concentration [$Pb^{2+}$]), the electrode potential was immediately switched to −0.8 V vs. Ag/AgCl for 50 s to measure the hydrogen evolution current (Im). Stripping coulometry was employed to strip the underpotentially deposited lead at an applied potential of −0.2 V vs. Ag/AgCl for 50 s to recover the bare copper surface. The hydrogen evolution baseline current (Ib) on the blank (Pb-free) Cu substrate was then measured at an applied potential of −0.8 V vs. Ag/AgCl for 50 s; (v) The change in hydrogen evolution current $\Delta I=Ib-Im$ was calculated. $\Delta I$ is related to the hydrogen evolution suppression due to underpotentially deposited lead and thus is a measure of the lead concentration in the test solution. For a given UPD time, higher $Pb^{+2}$ concentration in the sample solution will provide a larger $Pb_{UPD}$ coverage on Cu, and thus a larger suppression of the hydrogen evolution current.

Figure 3:
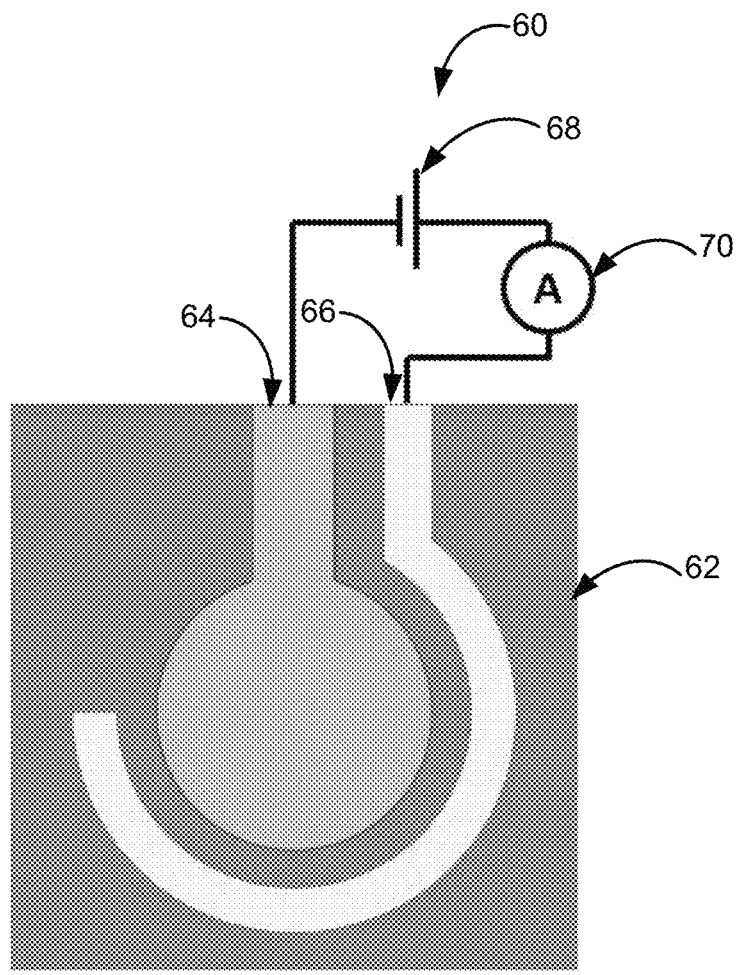
FIG. 3 is a schematic of the electrochemical sensor chip in accordance with an embodiment described herein. The center circular electrode is a copper working electrode and the surrounding concentric electrode is a platinum counter electrode. The two electrodes are connected to an external power supply and an ammeter.

In some embodiments, as shown in FIG. 3 the sensor 60 can include a substrate 62, a copper working electrode 64 formed on a surface of the substrate 62, and a counter electrode 66 formed on the surface of the substrate 62. The counter electrode 66 can include a metalized film, such as gold, platinum, palladium, silver, carbon, alloys thereof, and composites thereof. The films used to form the working electrode 64, counter electrode 66, and optional reference electrode (not shown) can be provided on the surface of the substrate 62 by using a thin film, thick film, and/or ink-jet printing technique, especially for the deposition of multiple electrodes on a substrate. The thin film process can include physical or chemical vapor deposition.

External power supply 68 and ammeter 70 can be incorporated together with essential automation in a handheld sensor (not shown) that can work autonomously. The two electrodes can be incorporated into a one-time use chip that can be attached to the handheld device.

In some embodiments, the working electrode, counter electrode, and optional reference electrode may be formed using laser ablation, a process which can produce elements with features that are less than one-thousandth of an inch. Laser ablation enables the precise definition of the working electrode, counter electrode, and reference electrode as well as electrical connecting leads and other features, which is required to reduce coefficient of variation and provide accurate measurements. Metalized films, such as Cu, Au, Pd, and Pt or any metal having similar electrochemical properties, that can be sputtered or coated on plastic substrates, such as PET or polycarbonate, or other dielectric material, can be irradiated using laser ablation to provide these features.

Figure 4A:
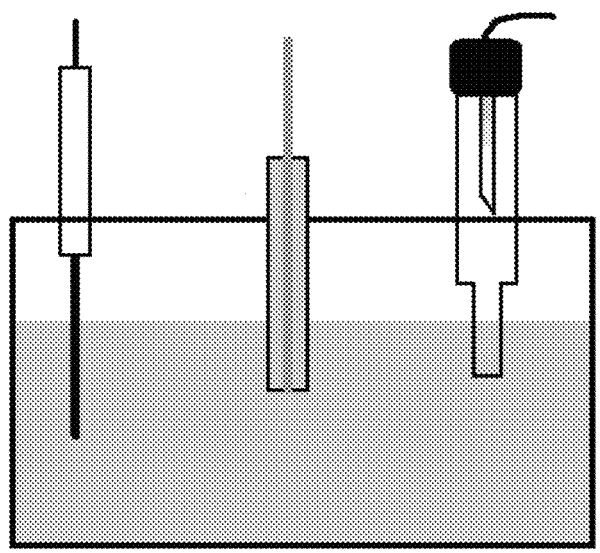
FIGS. 4(A-C) are schematic illustrations of a method of forming a copper working electrode having a needle-like dendrite surface profile.
Figure 4B:
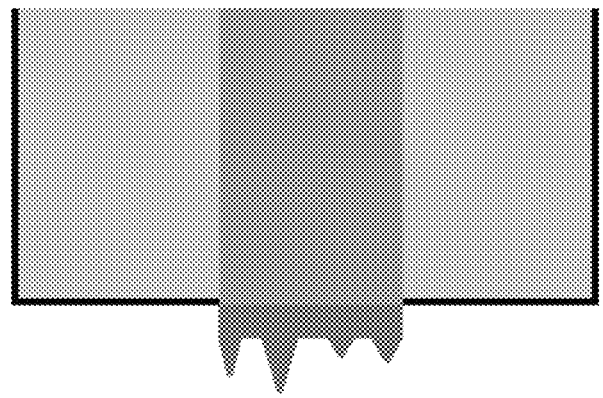
Figure 4C:
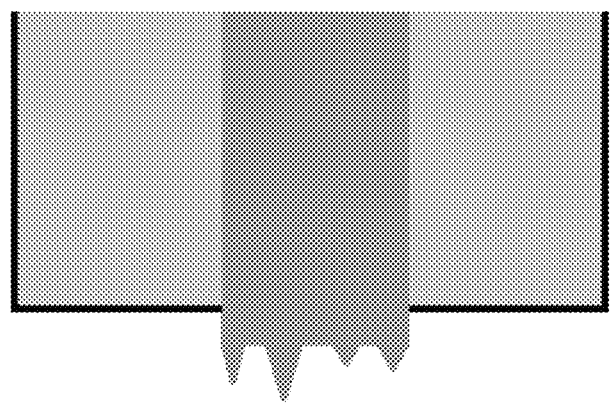

In some embodiments, in order to decrease the lead sensing time of the sensor, the copper working electrode can have an irregular needle-like dendrite surface profile as opposed to a planar surface. As illustrated in FIGS. 4(A-C), the irregular needle-like dendrite surface profile can be provided on a planar copper working electrode by placing a copper working electrode having a planar surface, a zinc counter electrode, and a Hg/HgO reference electrode in a 0.1 ZnO and KOH electrolyte (FIG. 4A). Zinc needle-like dendrites are then are then formed on the copper working electrode surface by zinc dentrite potentiostatic electroplating (e.g., −1.6V v. Hg/HgO for 500 s) (FIG. 4B). The zinc dendrite plated copper working electrode, counter electrode, and reference electrode are provided in a Cu electroplating solution and a copper layer is electroplated on the zinc dendrites to provide a working electrode with a copper needle-like dendrite surface profile (FIG. 4C).

Figure 5:
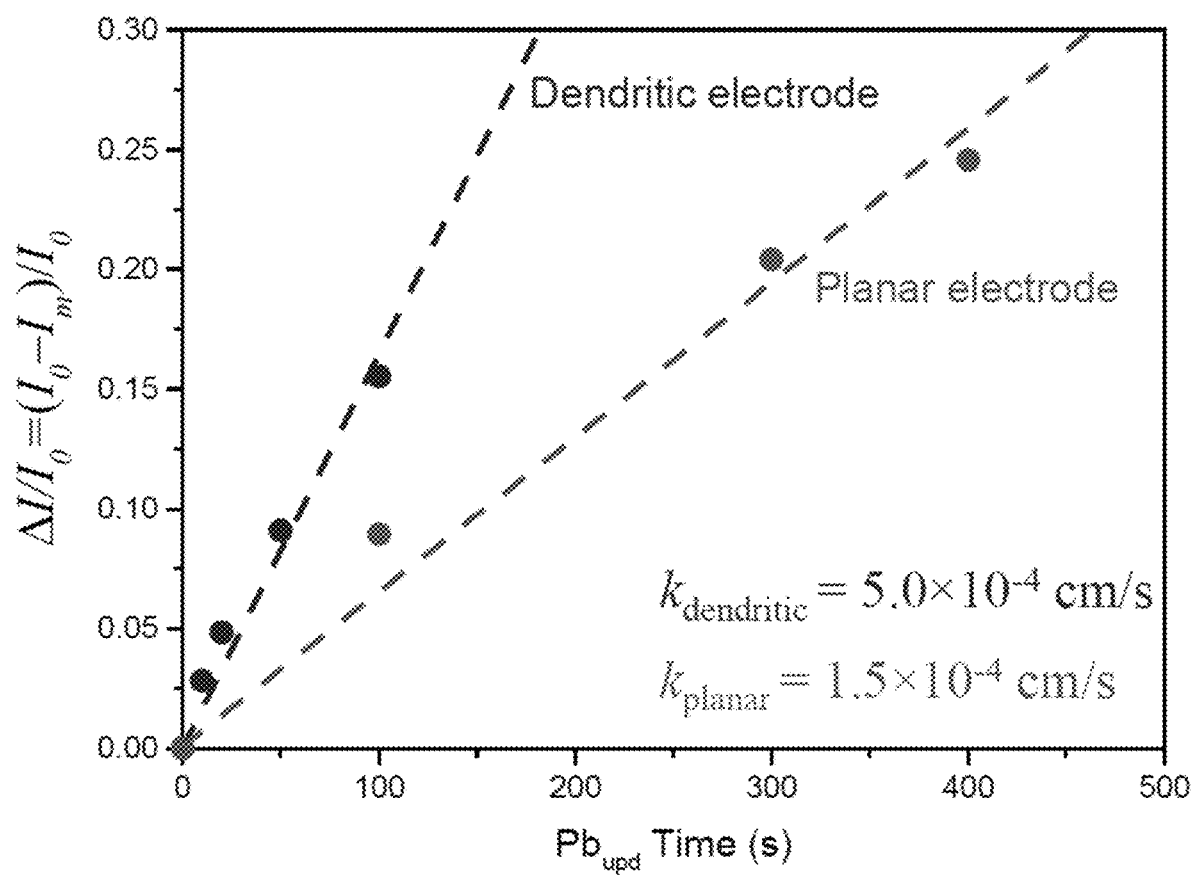
FIG. 5 illustrates a chart comparing hydrogen evolution current $\Delta I/I_0$ relative to the Pb under potential deposition time $t_{upd}$ for an aqueous 10 mM $HCLO_4$ and 1 ppm Pb2+ solution detected using a copper working electrode with needle-like dendrite surface profile and a copper working electrode with a planar surface profile.

FIG. 5 illustrates a chart comparing hydrogen evolution current $\Delta I/I_0$ relative to the Pb under potential deposition time $t_{upd}$ for an aqueous 10 mM $HClO_4$ and 1 ppm Pb2+ solution detected using a copper working electrode with needle-like dendrite surface profile and a copper working electrode with a planar surface. The chart shows the copper working electrode having an irregular needle-like dendrite surface profile compared to a planar surface has a decreased lead sensing time with an increased rate constant $k_{dendritic}$ of $5.0 \times 10^{-4}$ cm/s compared to $k_{planar}$ of $1.5 \times 10^{-4}$ cm/s.

The Example that follows illustrates embodiments of the present invention and are not limiting of the specification and claims in any way.

EXAMPLE

In this Example, we developed an electrochemical lead (Pb) sensor based on the principle of lead underpotential deposition ($Pb_{upd}$). Pb exhibits UPD on copper (Cu). At suitable electrode potentials, a Cu electrode can be coated with a monolayer of $Pb_{upd}$. The $Pb_{upd}$ surface coverage on Cu depends on the UPD time ($t_{upd}$) and the $Pb^{2+}$ concentration. The $Pb_{upd}$ layer when formed on Cu, depending on its coverage ($\theta$), suppresses the hydrogen evolution reaction (HER) current. The extent of HER suppression provides reliable quantification of the Pb surface coverage and thus the $Pb^{2+}$ concentration in solution. In this Example, we report the feasibility of this sensing concept for detecting $Pb^{2+}$ in the 10 ppb range in aerated electrolytes.

Deposition of $Pb_{upd}$ on Cu $Pb_{upd}$ deposition was performed in a three-electrode setup comprised of a sputter-deposited Cu substrate as the working electrode (area=1 cm$^2$), a saturated Ag/AgCl (Fisher Scientific) reference electrode, and a Pt wire as counter electrode. The Cu substrate was pretreated in acid (2M $H_2SO_4$) for 60 s followed by a DI water rinse. An electrolyte containing 10 mM perchloric acid ($HClO_4$, Fisher Scientific) and various concentrations (10 ppb, 100 ppb and 1 ppm) of lead perchlorate [$Pb(ClO_4)_2$, 99% purity, Acros Organics] was employed. The electrolyte was prepared using 18 MΩ-cm DI water. Such an electrolyte, although idealized compared to actual water samples, was deemed appropriate for demonstrating the basic sensor operation. For $Pb_{upd}$ characterization, the electrolyte was de aerated; however, for $Pb^{2+}$ detection, de-aeration was not applied. $Pb_{upd}$ was performed on Cu at an applied potential of −0.4 V vs. Ag/AgCl for various time periods ($t_{upd}$). To quantify the coverage of $Pb_{upd}$ on Cu, anodic stripping coulometry was used in which the $Pb_{upd}$ layer was potentiostatically stripped at −0.2 V vs. Ag/AgCl for 50 s and the net stripping charge density (Q) was measured.

Figure 6A:
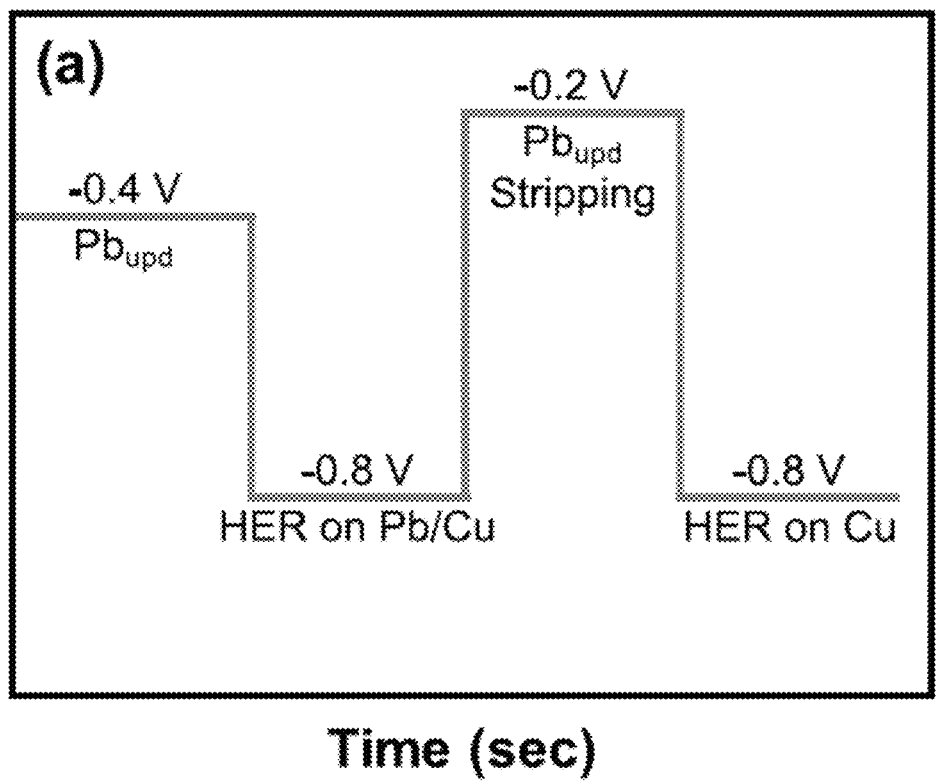
FIGS. 6(A-B) are plots showing operation of the electrochemical $Pb^{2+}$ sensor. The applied electrode potential (A) and the measured current response (B) are shown.

Measurement of the HER Current on $Pb_{upd}$-Modified Cu for Quantifying $Pb^{2+}$ Concentration In aerated electrolytes, $Pb_{upd}$ deposition on Cu was followed by measurement of the HER current. Sensor operation consisted of the following stepwise sequence (FIG. 6) implemented in electrolytes containing $Pb^{2+}$ in the 10 ppb-1 ppm range:

(i) $Pb_{upd}$ deposition onto Cu at −0.4 V vs. Ag/AgCl for $t_{upd}$ ranging from 100-30000 s.

(ii) Measurement of the HER current ($I_m$) on $Pb_{upd}$-modified Cu by switching the applied potential to −0.8 V vs. Ag/AgCl and allowing the HER current to reach steady-state in 50 s. Note that, at −0.8 V, background currents due to Pb deposition and $O_2$-reduction (ORR) may be present but these do not affect sensing as discussed below.

Figure 6B:
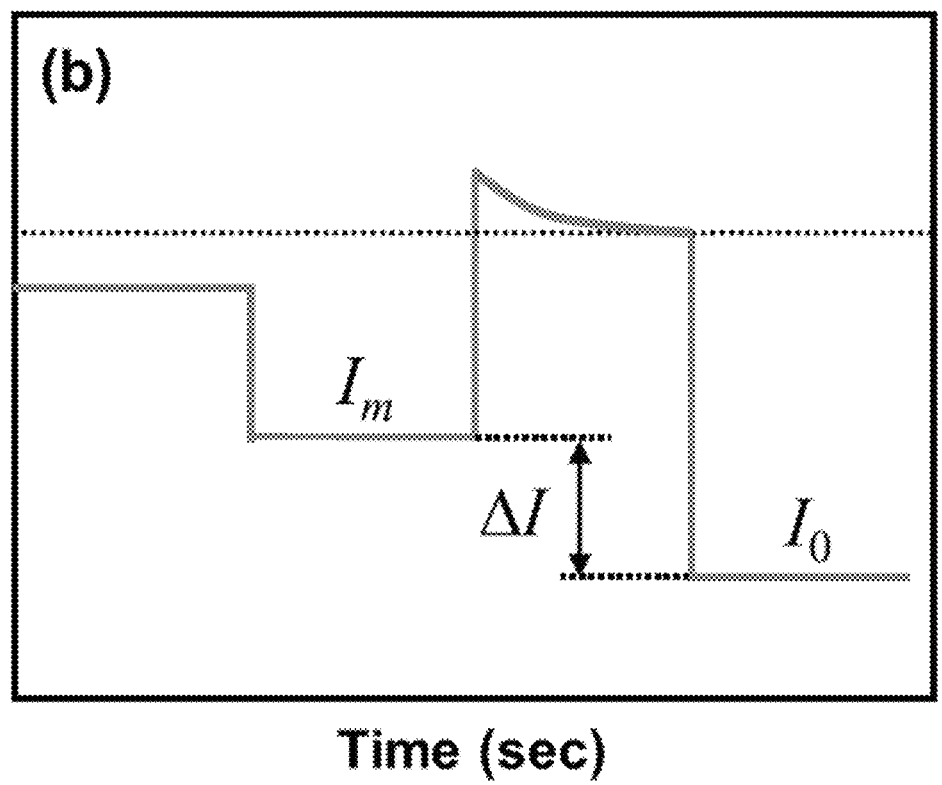

(iii) Stripping of the $Pb_{upd}$ layer formed in (i) at −0.2 V vs. Ag/AgCl to recover the bare Cu surface, followed by measurement of the HER current ($I_0$) on the bare Cu at −0.8 V. The current response to switching of the potential in steps (i)-(iii) is schematically shown in FIG. 6B. After implementing steps (i)-(iii), the change in HER current $\Delta I$ is computed:

$$\Delta I = I_0 - I_m \qquad [1]$$

$\Delta I$ represents the suppression of HER due to the presence of underpotentially deposited Pb on the Cu electrode. As $Pb_{upd}$ time in step (i) increases, the Pb coverage $\theta$ also increases and this causes an increase in $\Delta I$. The concentration dependence of this $\Delta I$–$t_{upd}$ relationship is the foundational principle of operation of the sensor.

Results

Characteristics of $Pb_{upd}$ Formation on Cu

Figure 7:
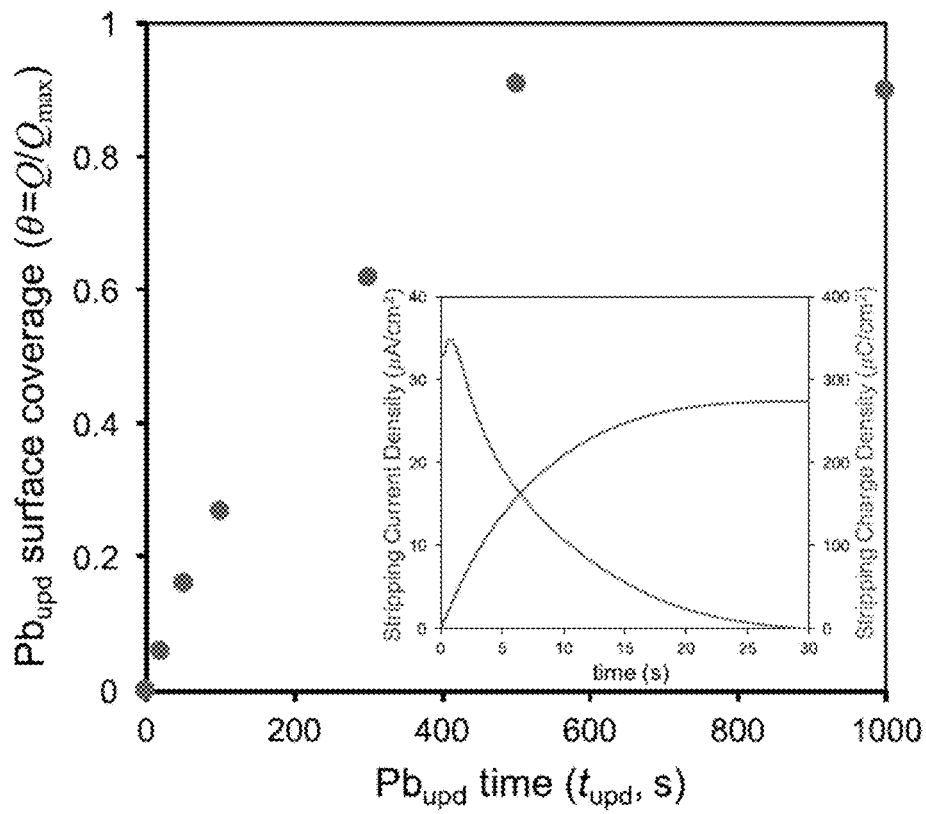
FIG. 7 illustrates $Pb_{upd}$ surface coverage (θ) increases linearly with $t_{upd}$ until surface saturation is reached at ~500 s. Inset shows the current (left axis) and charge (right axis) transients recorded during $Pb_{upd}$ stripping from which θ can be computed using Eq. [2].

FIG. 7 shows the dependence of $Pb_{upd}$ coverage on deposition time at −0.4 V vs. Ag/AgCl for an electrolyte containing 1 ppm of $Pb^{2+}$. The coverage $\theta$ was calculated by stripping the $Pb_{upd}$ layer, measuring the stripping charge density (Q, as shown in FIG. 3 inset), and then applying the equation:

$$\theta = \frac{Q}{Q_{max}} \qquad [2]$$

where $Q_{max}$ represents the charge density associated with saturation surface concentration of $Pb_{upd}$ where all surface sites available for UPD are occupied (about 300 μC/cm$^2$). FIG. 3 shows that $\theta$ increases linearly with time at short times (t<100 s) and $\theta$ reaches saturation at long times (t>500 s). The time-dependence of $\theta$ is related to diffusion and surface reaction rates, and thus is affected by the $Pb^{2+}$ concentration in solution.

HER Suppression on $Pb_{upd}$-Modified Cu

Figure 8:
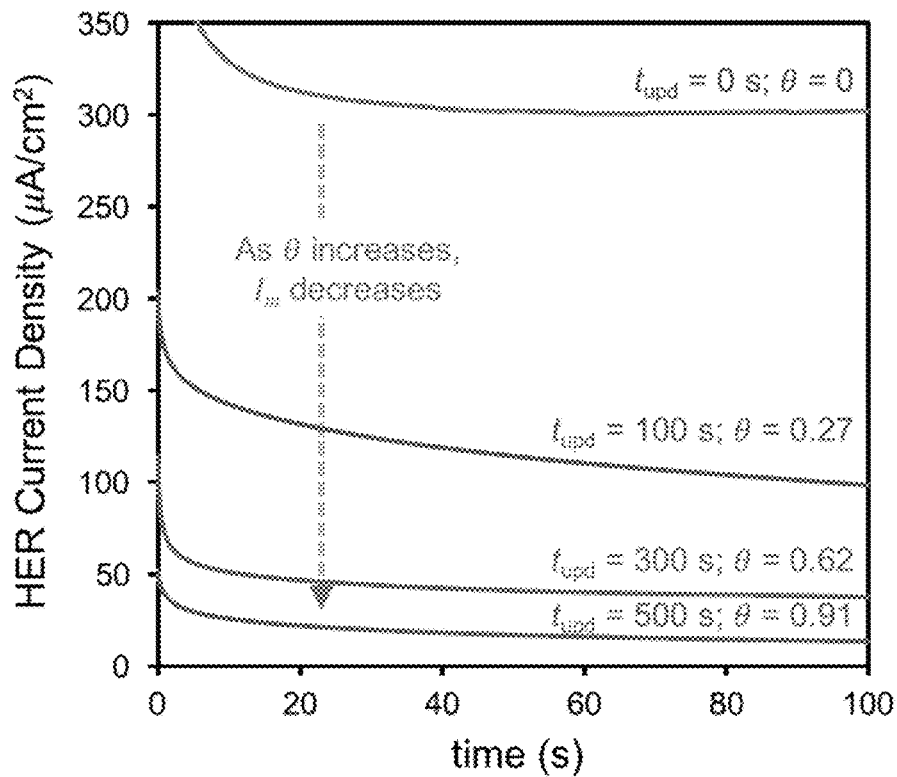
FIG. 8 illustrates the HER current ($I_m$) decreases as the $Pb_{upd}$ coverage increases. $Pb^{2+}$ concentration was 1 ppm.

As $Pb_{upd}$ covers the Cu surface, it suppresses $H_2$ evolution because of the very low exchange current density for HER on Pb. FIG. 8 shows HER current densities (at −0.8 V) on $Pb_{upd}$-modified Cu where the $Pb_{upd}$ was performed for $t_{upd}$=0, 100, 300 and 500 s from a 1 ppm $Pb^{2+}$-containing solution. It is noted that HER current density drops from 300 μA/cm$^2$ for $t_{upd}$=0 s (i.e., $\theta$=0) to merely 30 μA/cm2 for $t_{upd}$=500 s (i.e., $\theta$=0.91 from FIG. 7). The suppression of HER current is thus an indirect measure of the Pb coverage. For a fixed $t_{upd}$, the Pb coverage is in turn a function of the $Pb^{2+}$ concentration, as discussed below. A benefit of measuring HER current at a potential of −0.8 V is that its magnitude (~300 μA/cm$^2$ on bare Cu) is at least ten times larger than currents due to competing reactions: (i) Electrodeposition of Pb may occur in parallel to HER; however, mass-transport limited Pb electrodeposition proceeds at a meagre ~1 μA/cm$_2$ current even at 1 ppm $Pb^{2+}$ in solution; and (ii) Even in the presence of dissolved $O_2$, the ORR current is 20-40 μA/cm$_2$. Thus, suppression of the high (~300 μA/cm2) HER current due to $Pb_{upd}$ formation is detectable even in the presence of such background currents.

Figure 9A:
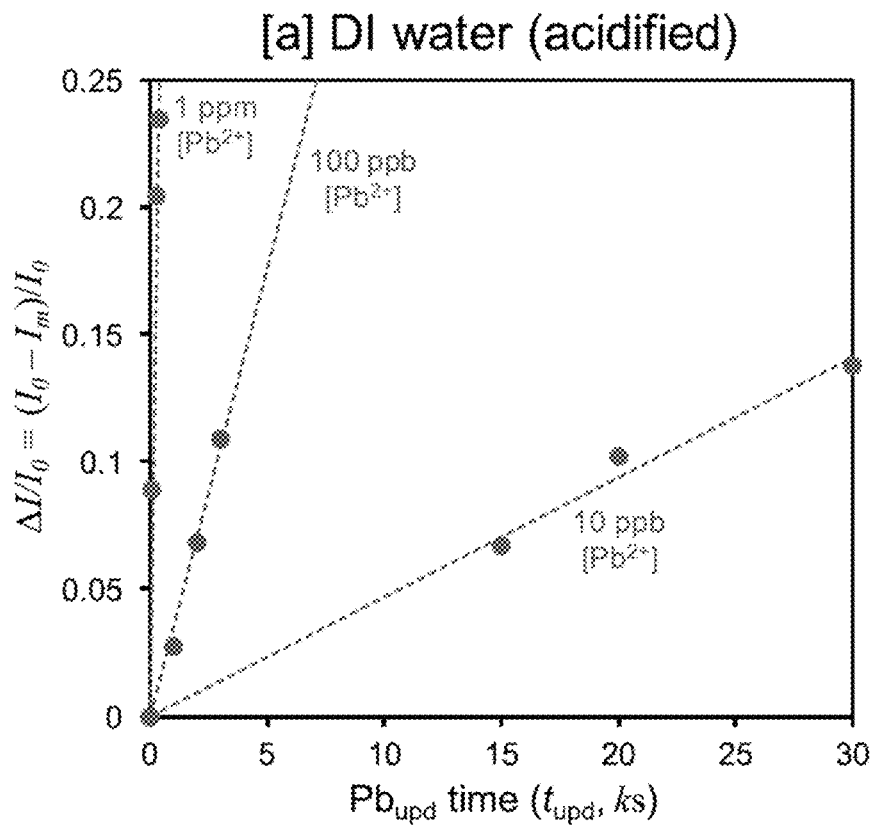
FIGS. 9(A-B) illustrate calibration charts showing the dependence of $\Delta I/I_0$ on $t_{upd}$ and $[Pb^{2+}]$ for (A) acidified DI water, and (B) acidified tap water. Insert in (B) shows that the electrochemical sensor provides $[Pb^{2+}]$ in actual tap water that is in close agreement with ICP-OES standards. For a fixed $t_{upd}$, $\Delta I/I_0$ can be measured and this enables determination of $[Pb^{2+}]$.
Figure 9B:
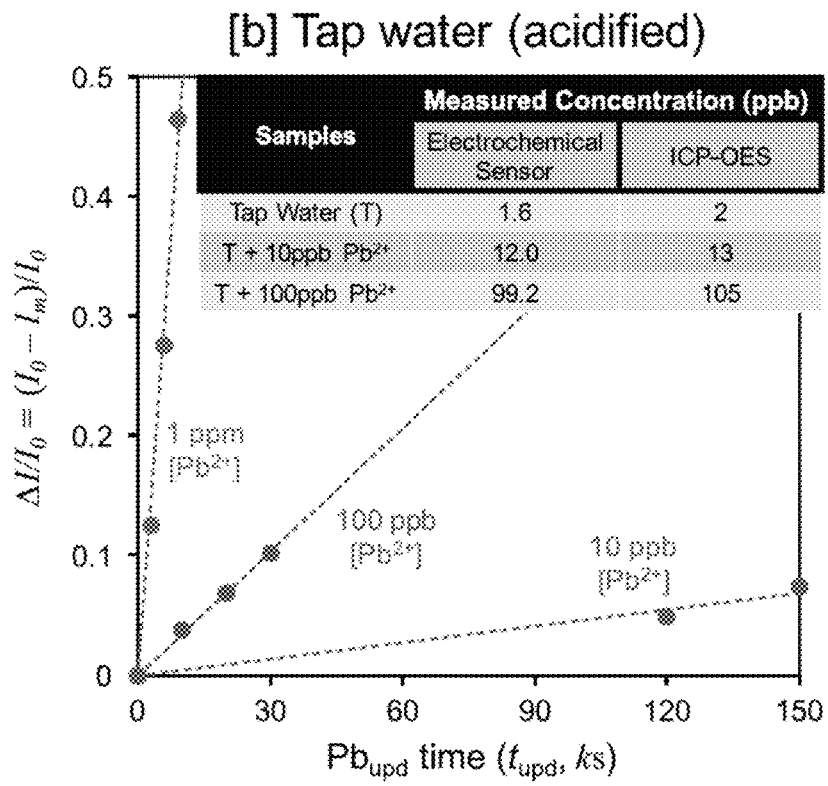

FIG. 9 shows the measured change in hydrogen evolution current ($\Delta I$) for aerated electrolytes with various concentrations of $Pb^{2+}$ (1 ppm, 100 ppb and 10 ppb). The ratio $\Delta I/I0$ is seen to be a linear function of $t_{upd}$ and is seen to depend on the $Pb^{2+}$ concentration. This provides a calibration chart for the electrochemical sensor. In an actual sensor, for a known value of $t_{upd}$ and a measured value of $\Delta I/I0$, a unique $Pb^{2+}$ concentration exists which can then be estimated from data in FIG. 9. Note that the linear dependence of $\Delta I/I0$ on $t_{upd}$ is measurable down to $Pb^{2+}$ concentration of 10 ppb which is the desired range for practical applications. Further, FIG. 9 was obtained in the absence of any de-aeration, which confirms that the sensing method functions even in the presence of background ORR currents.

Quantifying the Dependence of $\Delta I/I_0$ on $Pb^{2+}$ Concentration and $Pb_{upd}$ Time ($t_{upd}$)

As shown in FIG. 9, $\Delta I/I_0$ depends on the $Pb^{2+}$ concentration and on $t_{upd}$. We now examine this dependence quantitatively. Assuming the $Pb_{upd}$ formation process to be analogous to first-order surface adsorption, the time-dependent Pb surface coverage obeys:

$$\Gamma \frac{d\theta}{dt} = kC(1-\theta) \quad [3]$$

where $\Gamma$ is the Pb saturation surface concentration ($1.55 \times 10^{-9}$ mol/cm$^2$), Cb is the $Pb^{2+}$ concentration, and k is a rate constant. Initially (t=0), the coverage $\theta$=0. Furthermore, when $\theta$ is small, Eq. [3] yields:

$$\theta \cong \frac{kC_b}{\Gamma} t_{upd} \quad [4]$$

On $Pb_{upd}$-covered sites on the Cu electrode, the HER current is negligibly small. Thus, HER proceeds only on exposed Cu sites at a current given as:

$$I_m = I_0(1-\theta) \quad [5]$$

Combining Eqns. [1], [4] and [5], $\Delta I/I0$ exhibits the following dependence on $C_b$ and $t_{upd}$:

$$\frac{\Delta I}{I_0} = \left(\frac{kCb}{\Gamma}\right) t_{upd} \quad [6]$$

First, the linear dependence of $\Delta I/I0$ on $t_{upd}$ seen in Eq. [6] is consistent with experimental data (FIG. 9). Second, the slope of $\Delta I/I0$ vs. $t_{upd}$ is $kCb/\Gamma$, i.e., the slope increases linearly with the $Pb^{2+}$ concentration also consistent with FIG. 9. The measured slopes (from FIG. 9) for various $Pb^{2+}$ concentrations are listed in the Table. From these slopes, the rate constant k was estimated (Table) and found to be of the order $\sim 10^{-4}$ cm/s independent of $C_b$. This is significant because, for diffusion-limited adsorption, k approaches D/$\delta$, where D is the $Pb^{2+}$ diffusion coefficient ($\approx 10^{-5}$ cm$_2$/s) and $\delta$ is the boundary layer thickness (taken as 0.05 cm). For these estimated values of D and $\delta$, we get k=2×10−4 cm/s and thus within the same range as that measured experimentally (Table). This order of magnitude calculation establishes that the $Pb_{upd}$ step is limited by slow $Pb^{2+}$ diffusion, and thus this step may dictate the sensor response time especially when analyzing low ppb-levels of Pb.

TABLE

Analysis of $\Delta I/I0$ vs. $t_{upd}$ data presented in FIG. 9

| [Pb$^{2+}$] (ppb) | Slope of $\Delta I/I0$ vs. $t_{upd}$ (FIG. 5) | k (cm/s) |
|---|---|---|
| 10 | 4.68 × 10$^{-6}$ | 1.45 × 10$^{-4}$ |
| 100 | 3.67 × 10$^{-5}$ | 1.14 × 10$^{-4}$ |
| 1000 | 5.84 × 10$^{-4}$ | 1.81 × 10$^{-4}$ |

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of detecting lead in an aqueous sample, the method comprising:
    immersing a sensor in an aqueous sample, the sensor including a copper working electrode and a counter electrode;
    biasing the copper working electrode at a cathodic potential effective to facilitate underpotential deposition of a lead monolayer on a surface of the copper working electrode from the aqueous sample; and
    measuring a hydrogen evolution reaction (HER) current of the lead covered working electrode to determine the lead coverage and the lead concentration of the sample.

2. The method of claim 1, wherein the lead coverage and the lead concentration of the sample is determined by comparing the measured HER current of the lead covered working electrode to control value.

3. The method of claim 2, wherein the control value is a HER baseline current on lead-free working electrode.

4. The method of claim 3, further comprising stripping of the lead underpotential deposition layer formed to recover a lead-free, bare copper surface of the copper working electrode; and
    measuring the HER current on the bare copper working electrode.

5. The method of claim 1, wherein the counter electrode comprises gold, platinum, palladium, silver, carbon, or alloys thereof.

6. The method of claim 1, wherein the sensor further comprises a reference electrode.

7. The method of claim 1, wherein the copper working electrode has a needle-like dendritic surface profile.

8. The method of claim 1, wherein the needle-like dendritic surface profile of the copper working electrode is defined by an underlying Zn dendrite potentiostatic electroplate.

9. A method of detecting lead in an aqueous sample, the method comprising:
    immersing a sensor in an aqueous sample, the sensor including a copper working electrode and a counter electrode;
    biasing the copper working electrode at a cathodic potential effective to facilitate underpotential deposition of a lead monolayer on a surface of the copper working electrode from the aqueous sample; and
    measuring a hydrogen evolution reaction (HER) current of the lead covered working electrode by comparing the measured HER current of the lead covered working electrode to a HER baseline current on lead-free working electrode to determine the lead coverage and the lead concentration of the sample.

10. The method of claim 9, further comprising stripping of the lead underpotential deposition layer formed to recover a lead-free, bare copper surface of the copper working electrode; and measuring the HER current on the bare copper working electrode.

11. The method of claim 9, wherein the counter electrode comprises gold, platinum, palladium, silver, carbon, or alloys thereof.

12. The method of claim 9, wherein the sensor further comprises a reference electrode.

13. The method of claim 9, wherein the copper working electrode has a needle-like dendritic surface profile.

14. The method of claim 13, wherein the needle-like dendritic surface profile of the copper working electrode is defined by an underlying Zn dendrite potentiostatic electroplate.

* * * * *